United States Patent [19]

Ackerman

[11] Patent Number: 5,624,399
[45] Date of Patent: Apr. 29, 1997

[54] CATHETER HAVING AN INTRACERVICAL/INTRAUTERINE BALLOON MADE FROM POLYURETHANE

[75] Inventor: Bernard Ackerman, Metuchen, N.J.

[73] Assignee: Ackrad Laboratories, Inc., Cranford, N.J.

[21] Appl. No.: 536,682

[22] Filed: Sep. 29, 1995

[51] Int. Cl.⁶ ............................................. A61M 29/00
[52] U.S. Cl. ................ 604/96; 604/55; 604/174; 606/193; 606/119; 128/778; 128/658
[58] Field of Search ............................ 604/55, 176, 178, 604/53–54, 174, 96–103; 606/193, 192, 119; 128/778, 657, 658, 4–7

[56] References Cited

U.S. PATENT DOCUMENTS

| | | |
|---|---|---|
| 3,721,229 | 3/1973 | Panzer . |
| 4,088,135 | 5/1978 | O'Neill . |
| 4,182,328 | 1/1980 | Bolduc et al. . |
| 4,654,025 | 3/1987 | Cassou et al. . |
| 4,693,704 | 9/1987 | Ogita . |
| 4,952,357 | 8/1990 | Euteneuer . |
| 4,976,692 | 12/1990 | Atad . |
| 5,104,377 | 4/1992 | Levine . |
| 5,147,300 | 9/1992 | Robinson et al. . |
| 5,156,612 | 10/1992 | Pinchuk et al. . |
| 5,207,700 | 5/1993 | Euteneuer . |
| 5,223,205 | 6/1993 | Jackowski et al. . |
| 5,236,659 | 8/1993 | Pinchuk et al. . |
| 5,259,836 | 11/1993 | Thurmond et al. . |
| 5,264,260 | 11/1993 | Saab . |
| 5,290,306 | 3/1994 | Trotta et al. . |
| 5,304,197 | 4/1994 | Pinchuk et al. . |
| 5,330,428 | 7/1994 | Wang et al. . |
| 5,334,146 | 8/1994 | Ozasa . |
| 5,338,295 | 8/1994 | Cornelius et al. . |
| 5,344,400 | 9/1994 | Kaneko et al. . |
| 5,344,401 | 9/1994 | Radisch et al. . |
| 5,356,591 | 10/1994 | Pinchuk et al. . |
| 5,370,618 | 12/1994 | Leonhardt . |
| 5,372,584 | 12/1994 | Zink et al. . |

OTHER PUBLICATIONS

"Sonohysterography for Endometrial Abnormalities: Preliminary Results", by Anna K. Parsons, MD, and Jorge J. Lense, MD, J Clin Ultrasound 21:87–95, Feb. 1993 by John Wiley & Sons, Inc.

Primary Examiner—Randall L. Green
Assistant Examiner—Perry E. Van Over
Attorney, Agent, or Firm—Plevy & Associates

[57] ABSTRACT

A catheter for non-surgical entry into the cervical canal or the uterus, comprising an elongated tubular catheter body. An inflatable balloon manufactured from a polyurethane material is disposed proximal to the distal end of the catheter body. The polyurethane inflatable balloon can be progressively inflated into an elliptical shape which enables the balloon to be used within the cervical canal. Additional inflation pressure inflates the polyurethane inflatable balloon to a spherical shape which enables the balloon to be used within the uterus.

20 Claims, 3 Drawing Sheets

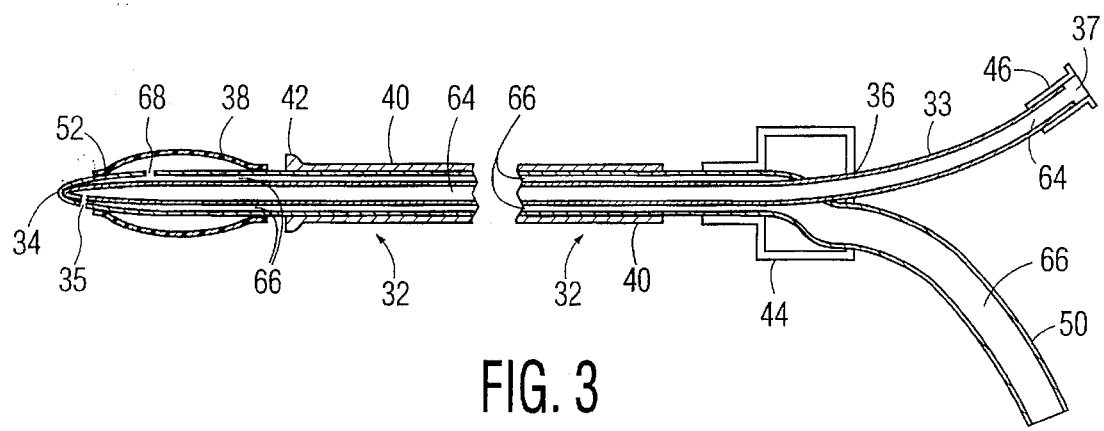
FIG. 3
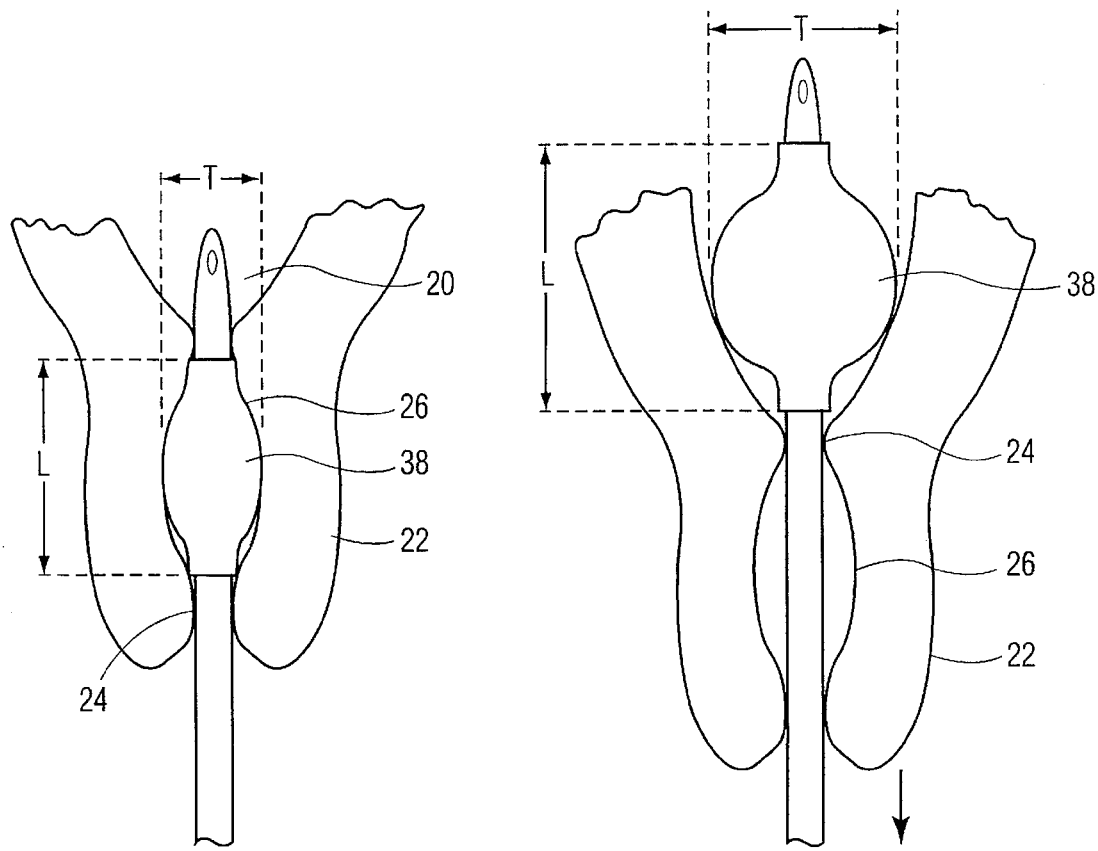
FIG. 4A
FIG. 4B

CATHETER HAVING AN INTRACERVICAL/ INTRAUTERINE BALLOON MADE FROM POLYURETHANE

FIELD OF THE INVENTION

The present invention relates generally to catheters and more particularly, to a catheter for non-surgical entry into the uterine cavity, having an inflatable intracervical/ intrauterine balloon made from polyurethane or poly(vinyl chloride).

BACKGROUND OF THE INVENTION

There are a number of well known diagnostic procedures which require a non-surgical entry into the uterus. One such procedure is called hysterosalpingography. Hysterosalpingography is a radiographic method that is used for imaging the anatomical structures of the uterus and fallopian tubes.

Hysterosalpingography generally can be carried out by the introduction of a fine flexible catheter into the cervical canal or uterus, to deliver a contrast medium, such as an iodinated fluid, into the uterus. Radiography is then carried out to provide the imaging information. Another well known diagnostic procedure which entails the non-surgical entry into the uterus is called sonohysterography. This procedure can also employ a fine flexible catheter that is inserted into the cervical canal or uterus. The catheter in this procedure enables the physician or technician to introduce a sterile saline solution into the uterus to expand it so that an ultrasound scanner can be used to sonographically observe the uterus.

In both procedures, the catheter used to introduce the diagnostic fluid into the uterus must also be capable of sealing off the uterus after introducing the fluid to prevent backflow into the vaginal canal. Further, the catheter must also be capable of being anchored in the uterus or cervix to prevent dislodgement of the catheter during the procedure.

Accordingly, prior art catheter assemblies include a catheter having an inflatable intrauterine balloon made generally from a latex material to seal the uterus and secure the catheter assembly to the uterus to prevent dislodgement during the procedure. One example of such a catheter assembly is shown in FIG. 1A, which shows a catheter 10 having an inflatable intrauterine balloon 14 inserted into the uterus 20. The catheter assembly shown therein is operated by deflating the intrauterine balloon 14 and inserting the distal tip 12 of the catheter 10 through the cervical canal 24 of the cervix 22 and into the uterus 20. The insertion of the distal tip 12 operates to position the deflated intrauterine balloon 14 in the uterus 20. Once positioned, the inflation syringe 16 is used to inflate the intrauterine balloon 14 and the catheter is retracted to place the balloon against the internal os or opening of the uterus. As can be seen in FIG. 1A, once inflated, the intrauterine balloon 14 seals the uterus 20 by blocking the opening leading to the cervical canal 24. A major disadvantage of this design, however, is that the inflated balloon 14 tends to block portions of the uterus during imaging making those portions unviewable.

In order to circumvent this problem, other prior art catheter assemblies as shown in FIG. 1B, have been designed so that the insertion of the distal tip 12 of the catheter 10 into the uterus 20 positions an intracervical balloon 14' in the large spindle-shaped portion 26 of the cervical canal 24. Thus, when the intracervical balloon 14' is inflated, it does not obstruct the uterus 20 during imaging and thereby, allows the entire uterus 20 to be viewed. In practice, however, it has been discovered that when the balloon 14' is inflated in the cervical canal 24, patients experience a considerable amount of pain because the cervix 22 has a large number of nerve endings which makes it very sensitive to the pressure caused by the inflation of the balloon. This problem is made worse by the latex material used in manufacturing these prior art balloons. As is well known in the art, catheter balloons made from latex inflate suddenly in a non-progressive or non-linear manner. The non-progressive inflation rate of balloon catheters made from latex is described in greater detail in U.S. Pat. No. 5,370,618 entitled PULMONARY ARTERY POLYURETHANE BALLOON CATHETER issued to Leonhardt. According to this patent, pulmonary artery balloon catheters made from latex inflate erratically and suddenly due to the relatively high tension of the latex material. This results in a surge to full size when the critical inflation pressure is reached. It is this sudden inflation of the intracervical balloon to full size in the spindle of the cervical canal which intensifies the pain experience by the patient. Moreover, because the inflation rate of the balloon is so sudden, the prior art intracervical balloons have a substantially spherical shape which does not match the ellipsoidal shape of the spindle of the cervical canal.

Further, neither one of the prior art catheters described above can be universally operated so that the balloon can be positioned in either the cervical canal or the uterus whichever is most desirable for a given diagnostic procedure. This necessitates having at least two different types of catheters on hand which is inconvenient and more costly.

It is, therefore, an object of the present invention to provide an improved catheter for non-surgical entry into the cervical canal or uterus, which has an inflatable intracervical/intrauterine balloon that can be inflated progressively in a linear manner to either a substantially elliptical shape or a substantially spherical shape. This provides a catheter that can be operated in either the cervical canal or the uterus.

SUMMARY OF THE INVENTION

A catheter for non-surgical entry into the cervical canal or the uterus, comprising an elongated tubular catheter body for insertion into the cervical canal or the uterus. An inflatable balloon manufactured from a polyurethane material is disposed proximal to the distal end of the catheter body. The polyurethane inflatable balloon can be progressively inflated into an elliptical shape which enables the balloon to be used within the cervical canal. Additional inflation pressure inflates the polyurethane inflatable balloon to a spherical shape which enables the balloon to be used within the uterus.

BRIEF DESCRIPTION OF THE DRAWINGS

For a detailed understanding of the present invention, reference should be made to the following detailed description taken in conjunction with the accompanying drawings wherein:

FIG. 3 is a lateral cross-sectional view of the catheter of the present invention;

FIG. 4A is representational view of the catheter of the present invention anchored in the cervical canal; and FIG. 4B is representational view of the catheter of the present invention anchored into the uterus.

DETAILED DESCRIPTION OF THE INVENTION

Figure 1A:
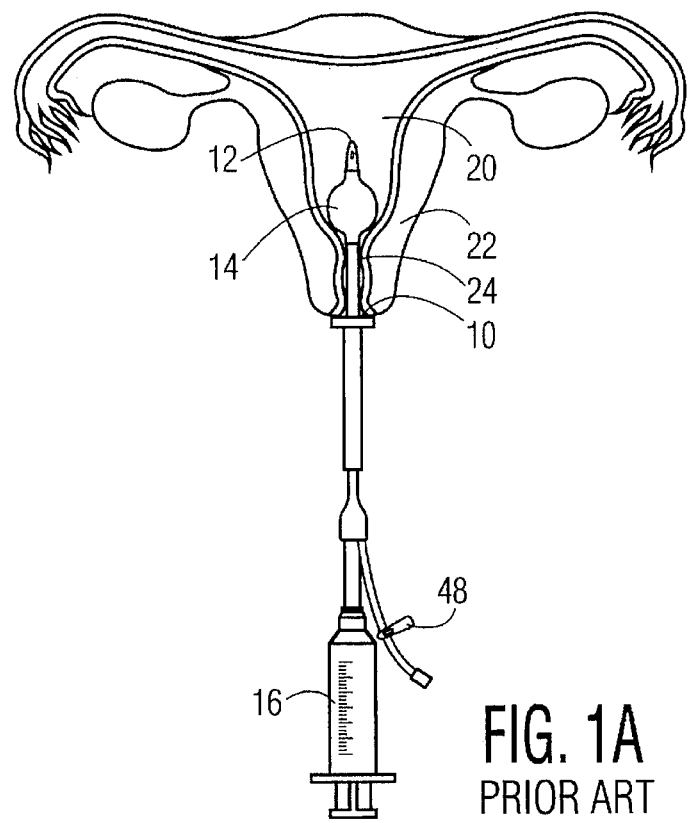
FIG. 1A is representational view of a prior art catheter anchored in the uterus.
Figure 1B:
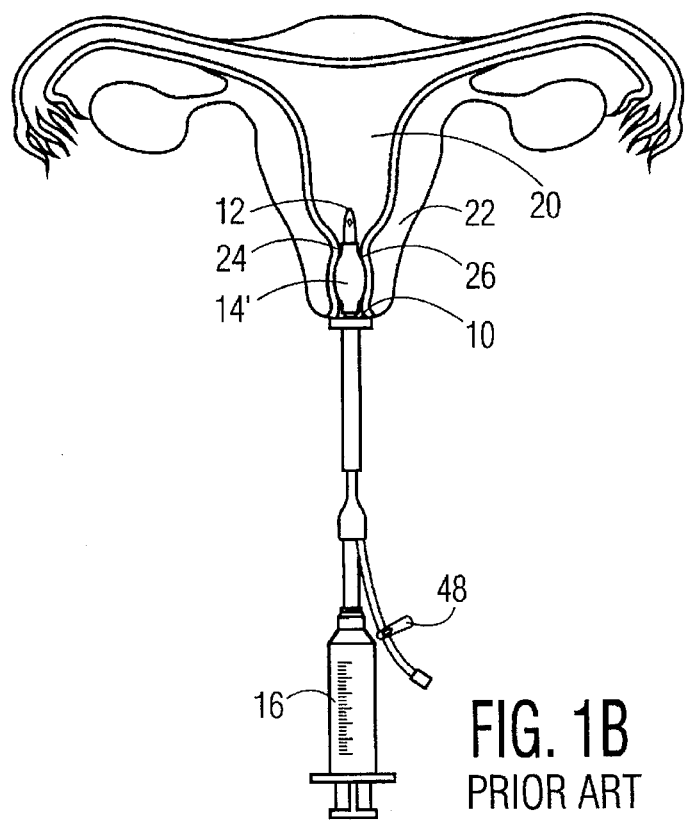
FIG. 1B is representational view of a prior art catheter anchored in the cervical canal.
Figure 2:
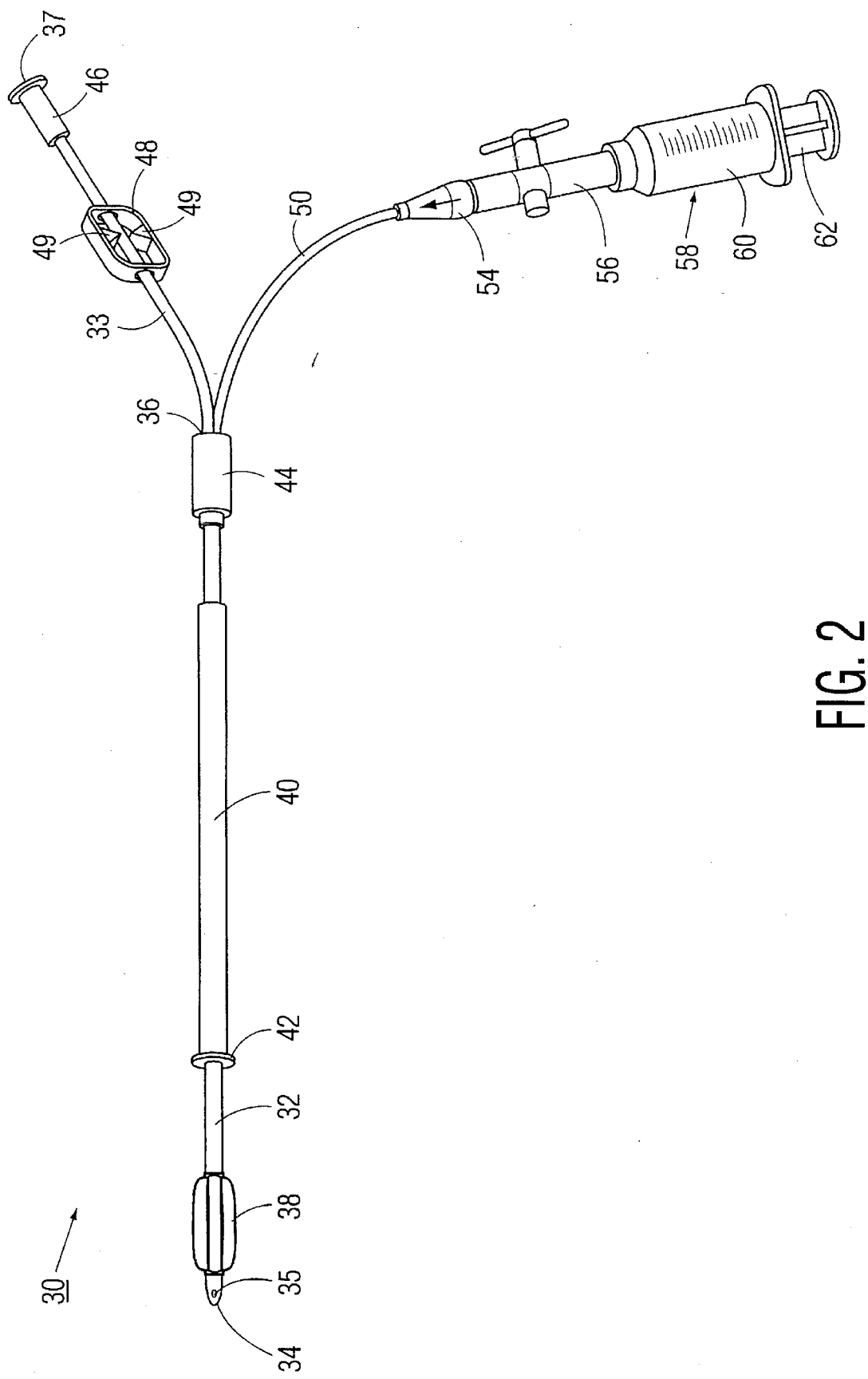
FIG. 2 is a perspective view of the catheter of the present invention.

Referring to FIG. 2, an exemplary embodiment of a catheter of the present invention is shown and generally designated by the numeral 30. The catheter 30 is primarily intended for non-surgical entry into the uterine cavity of a female although one of ordinary skill in the art will recognize its usefulness in other related procedures.

As shown in FIG. 2, the catheter 30 has an elongated tubular body 32 which extends from a distal end 34 to a proximal end 36. Located on the marginal distal end of the body 32 is an inflatable intracervical/intrauterine balloon 38 made from a polyurethane material. As can be seen, the balloon 38 is shown in the deflated state. A connector 46 for coupling various medical instruments to the catheter 30 is located at a proximal end 37 of a diagnostic fluid line 33 which will be described in greater detail later on. Slidably mounted on the fluid line 33 just before the connector 46 is a conventional locking plastic pinch clamp 48.

Still referring to FIG. 2, the catheter also includes an inflation fluid line 50 having a distal end 52 (see FIG. 3) which terminates within the body 32 and a proximal end 54. The inflation fluid line 46 enters the body 32 at a fluid line coupler 44. The proximal end 54 of the inflation fluid line 50 is coupled to a conventional inline rotary valve 56. The proximal end of the inline rotary valve 56 is removably coupled to a conventional inflation syringe 58. Also included on the catheter 30 is a cylindrical collar member 40, which is slidably mounted on the tubular body 32 between the balloon 38 and the fluid line coupler 44. The collar member includes a outwardly extending circumferential flange 42 at its distal end.

In FIG. 3, there is shown a lateral cross-sectional view of the catheter 30. As can be seen, the earlier described diagnostic fluid line 33 defines a working lumen 64, a major portion of which extends the entire length of the body 32 from the distal end 34 to the proximal end 36. The working lumen 64 of the diagnostic fluid line 33 provides a fluid communication path for the introduction of a diagnostic fluid into the uterine cavity. The pinch clamp 48 (see FIG. 2) described earlier operates to occlude the working lumen 64 after a diagnostic fluid has been introduced into the lumen of the catheter before insertion into the uterine cavity in order to minimize air being injected. This is accomplished by squeezing the pinch clamp 48 into the "locked pinch mode". Opposing projections 49 on the pinch clamp 48 operate on the diagnostic fluid line 33 to occlude the working lumen 64. It should be understood that the structure and operation of such pinch clamps are well known in the art and needn't be describe here in any greater detail.

Still referring to FIG. 3, the distal end 52 of the inflation fluid line 50 defines an inflation lumen 66. As can be seen, the inflation lumen 66 starts at the proximal end of the inflation fluid line 50 and extends therethrough to the distal end 52 thereof. The inflation lumen 66 communicates with the interior of balloon 38 via an aperture 68. The inflation lumen 66 of the inflation fluid line 50 provides a communication path for inflating the balloon 38 with either saline or air. The earlier described inline rotary valve 56 operates to maintain the balloon in the inflated state after inflation by the inflation syringe 58. In operation, the balloon 38 is inflated by pushing the plunger 60 into the body 62 of the inflation syringe 58 (see FIG. 2). Once the balloon 38 is inflated, the inline rotary valve 56 is rotated into the "closed position" which prevents communication between the inflation syringe 58 and the inflation lumen 66. When it is desirable to deflate the balloon 38, the inline rotary valve is rotated into the "open position" which reestablishes communication between the inflation syringe 58 and the inflation lumen 66. To deflate the balloon 38, the plunger 60 is pulled toward the proximal end of the body 62 of the inflation syringe 58.

All the components of the catheter 30 of the present invention are made from conventional materials such as nylon, polyethylene, or a composite. The intracervical/intrauterine balloon 38 is made from a polyurethane and other material having a Shure A durometer of between approximately 70 and 95. The balloon 38 of the present invention can be placed in the cervix 22 to occlude the cervical canal 24 as shown in FIG. 4A or placed in the uterus 20 as shown in FIG. 4B, to block the opening, or internal os leading to the cervical canal 24. This is made possible by the novel construction of the balloon 38 which enables it to be progressively transformed from an ellipsoidal shape as shown in FIG. 4A to a spherical shape as shown in FIG. 4B with increasing inflation pressure. This is made possible by fabricating the balloon 38 from a polyurethane material and attaching it to the body 32 of the catheter 30 so that the longitudinal axis L of the balloon is longer than the transverse axis T of the balloon upon initial inflation. This produces a balloon that is substantially elliptical in shape shown in FIG. 4A. Accordingly, the ellipsoidal shape of the balloon 38 matches the natural shape of the spindle 26 of the cervical canal 24. The progressive inflation characteristics and the elliptical shape of the balloon 38 of the catheter of the present invention enable it to be used to occlude the cervical canal with minimal pain, compared to conventional prior art spherical-shaped latex intracervical balloons.

Further, the balloon 38 can be progressively inflated to a substantially spherical shape with additional inflation pressure. More specifically, additional inflation pressure increases only the transverse axis T of the balloon 38 which results in a balloon with a substantially spherical shape. When the balloon 38 is so inflated, it can now be used in the uterus to block the opening leading to the cervical canal 24 if desired as shown in FIG. 4B.

The balloon 38 can be molded or extruded using well known methods and techniques. In the exemplary embodiment, the preferred wall thickness of the balloon 38 in the deflated state should be between 0.001 to 0.003 inches. The balloon 38 can be attached to the body 32 of the catheter 30 using any well known method such as adhesive bonding, heat sealing, and/or mechanically clamped.

In order to demonstrate the progressive transformation from an elliptical configuration to a spherical configuration, increasing amounts of air were injected into the balloon 38 of the present invention and measurements of the transverse axis T and the Longitudinal axis L were taken. All measurements were made on a 1.67 mm diameter catheter using precision calipers. The results are listed in Table 1 below.

| cc of Air | Transverse axis T mm | Longitudinal axis L mm |
| --- | --- | --- |
| 0.2 | 6.2 | 14.7 |
| 0.4 | 8.2 | 15.1 |
| 0.6 | 9.0 | 15.3 |
| 0.8 | 9.9 | 14.9 |
| 1.0 | 10.6 | 14.9 |

| cc of Air | Transverse axis T mm | Longitudinal axis L mm |
| --- | --- | --- |
| 1.5 | 12.1 | 15.0 |
| 2.0 | 13.2 | 15.0 |
| 2.5 | 13.9 | 14.8 |
| 3.0 | 14.5 | 15.3 |
| 3.5 | 14.9 | 15.3 |

Although the test data listed above is for polyurethane, other elastomeric materials can also operate in a similar manner such as poly(vinyl chloride) and so on.

It should be understood that the embodiment described herein is merely exemplary and that a person skilled in the art may make many variations and modifications to the embodiment utilizing functionally equivalent elements to those described herein. Any and all such variations or modifications as well as others which may become apparent to those skilled in the art, are intended to be included within the scope of the invention as defined by the appended claims.

I claim:

1. A catheter for non-surgical entry into the cervical canal or the uterus, comprising:

an elongated tubular catheter body for insertion into the cervical canal or the uterus, said catheter body having a distal end and a proximal end; and an inflatable balloon manufactured from a polyurethane material disposed adjacent to said distal end of said catheter body, wherein said inflatable balloon can be progressively inflated into a first predetermined shape which is operative within the cervical canal and a second predetermined shape which is operative within the uterus.

2. The catheter according to claim 1, wherein said first predetermined shape is substantially elliptical.

3. The catheter according to claim 1, wherein said second predetermined shape is substantially spherical.

4. The catheter according to claim 1, wherein said catheter body includes a lumen which extends from said distal end to said proximal end and provides a fluid communication path for the introduction of a diagnostic fluid into the uterus.

5. The catheter according to claim 4, further comprising clamping means located marginally adjacent to said proximal end of said catheter body for selectively occluding said lumen.

6. The catheter according to claim 1, further comprising:

an inflation fluid line having a distal end and a proximal end, said distal end of said inflation fluid line communicating with an interior of said balloon; and means for inflating said balloon coupled to said proximal end of said inflation fluid line.

7. The catheter according to claim 6, wherein said inflation fluid line defines a lumen which provides a communication path for inflating and deflating said balloon with said means for inflating.

8. The catheter according to claim 6, wherein said means for inflating comprises an inflation syringe.

9. The catheter according to claim 8, wherein said means for inflating further comprises valve means coupled between said proximal end of said inflation fluid line and said inflation syringe.

10. A catheter for non-surgical entry into the cervical canal or the uterus, comprising:

an elongated tubular catheter body for insertion into the cervical canal or the uterus, said catheter body having a distal end and a proximal end;

an inflatable balloon manufactured from a polyurethane material disposed adjacent to said distal end of said catheter body, wherein said inflatable balloon can be progressively inflated into a first predetermined shape which is operative within the cervical canal and a second predetermined shape which is operative within the uterus;

a diagnostic fluid line extending from said distal end to said proximal end of said catheter body for providing a fluid communication path for the introduction of a diagnostic fluid into the uterus; and an inflation fluid line communicating with an interior of said balloon for providing a communication path for inflating and deflating said balloon, wherein a portion of said inflation fluid line extends coaxially with said diagnostic fluid line through said catheter body.

11. The catheter according to claim 10, wherein said first predetermined shape is substantially elliptical.

12. The catheter according to claim 11, wherein said second predetermined shape is substantially spherical.

13. The catheter according to claim 10, wherein said second predetermined shape is substantially spherical.

14. The catheter according to claim 10, further comprising clamping means located marginally adjacent to a proximal end of said diagnostic fluid line for selectively occluding said diagnostic fluid line.

15. The catheter according to claim 10, further comprising means for inflating said balloon coupled to a proximal end of said inflation fluid line.

16. The catheter according to claim 15, wherein said means for inflating comprises an inflation syringe and valve means coupled between said proximal end of said inflation fluid line and said inflation syringe.

17. A method for introducing a diagnostic fluid into the uterus, comprising the steps of:

providing a catheter having an elongated tubular catheter body for insertion into the cervical canal or the uterus, said catheter body having a distal end and a proximal end, and an inflatable balloon manufactured from a polyurethane material disposed adjacent to said distal end of said catheter body that can be progressively inflated into a first predetermined shape and a second predetermined shape;

deflating said balloon;

inserting said distal end of said catheter into the cervical canal;

inflating said balloon to said first predetermined shape to occlude the cervical canal to prevent the loss of a diagnostic fluid to be introduced into the uterus; and passing the diagnostic fluid through said catheter body and into said uterus.

18. The method according to claim 17, wherein said first predetermined shape is substantially elliptical and said second predetermined shape is substantially spherical.

19. The method according to claim 17, wherein after said step of inflating, said method further comprises the steps of:

deflating said balloon and relocating said distal end of said catheter body in the uterus; and inflating said balloon to said second predetermined shape to block the opening of the cervical canal to prevent loss of said diagnostic fluid.

20. The method according to claim 19, wherein said first predetermined shape is substantially elliptical and said second predetermined shape is substantially spherical.

* * * * *